(12) United States Patent
Bolognia

(10) Patent No.: US 9,332,940 B1
(45) Date of Patent: May 10, 2016

(54) COMPACT WEARABLE BIOLOGICAL SENSOR MODULES

(71) Applicant: ANALOG DEVICES, INC., Norwood, MA (US)

(72) Inventor: David Frank Bolognia, North Andover, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 0 days.

(21) Appl. No.: 14/589,685

(22) Filed: Jan. 5, 2015

(51) Int. Cl.
| *A61B 5/00* | (2006.01) |
| *A61B 5/024* | (2006.01) |
| *A61B 5/11* | (2006.01) |

(52) U.S. Cl.
CPC ........... *A61B 5/6802* (2013.01); *A61B 5/02438* (2013.01); *A61B 5/11* (2013.01); *A61B 2560/0214* (2013.01); *A61B 2560/0412* (2013.01); *A61B 2562/16* (2013.01); *A61B 2562/227* (2013.01)

(58) Field of Classification Search
USPC ......................................................... 235/487
See application file for complete search history.

(56) References Cited

U.S. PATENT DOCUMENTS

| 4,862,153 | A | 8/1989 | Nakatani et al. |
| 6,061,245 | A | 5/2000 | Ingraham et al. |
| 6,238,338 | B1 | 5/2001 | DeLuca et al. |
| 6,426,240 | B2 | 7/2002 | Isaak |
| 6,590,282 | B1 | 7/2003 | Wang et al. |
| 6,731,000 | B1 | 5/2004 | Haque et al. |
| 6,841,855 | B2 | 1/2005 | Jaeck et al. |
| 6,884,653 | B2 | 4/2005 | Larson |
| 7,081,373 | B2 | 7/2006 | Roeters et al. |
| 7,291,907 | B2 | 11/2007 | RaghuRam |
| D557,423 | S | 12/2007 | Chen |
| D643,929 | S | 8/2011 | DelloStritto et al. |
| 8,280,682 | B2 | 10/2012 | Vock et al. |
| D701,964 | S | 4/2014 | Yoneta et al. |
| 8,750,954 | B2 | 6/2014 | Petersen et al. |
| 8,750,974 | B2 | 6/2014 | Baker et al. |
| 2004/0238936 | A1 | 12/2004 | Rumer et al. |
| 2005/0012199 | A1 | 1/2005 | Rosenau et al. |
| 2006/0033217 | A1 | 2/2006 | Taggart et al. |
| 2006/0091508 | A1 | 5/2006 | Taggart et al. |
| 2007/0123756 | A1 | 5/2007 | Kitajima et al. |
| 2007/0270678 | A1 | 11/2007 | Fadem et al. |
| 2011/0255249 | A1 | 10/2011 | Lee et al. |
| 2012/0151758 | A1 | 6/2012 | Primavera |
| 2013/0183646 | A1* | 7/2013 | Lusted ............... A61B 5/164 434/236 |

(Continued)

*Primary Examiner* — Christle I Marshall
(74) *Attorney, Agent, or Firm* — Knobbe, Martens, Olson & Bear LLP

(57) ABSTRACT

A sensor module can include a battery housing comprising a battery cavity sized and shaped to receive a battery. The battery cavity can be defined at least in part by a wall to be disposed about at least a portion of a periphery of the battery. A package housing can be disposed on the wall of the battery housing, the package housing smaller than the battery housing. An integrated device package can be disposed in or coupled with the package cavity. The integrated device package can include one or more integrated device dies. An interfacing feature can be coupled with the battery housing and extending transverse to the wall. The interfacing feature can be configured to transduce a biological signature into a signal to be processed by the integrated device package. An interconnect assembly can electrically connect the interfacing feature to the integrated device package.

20 Claims, 12 Drawing Sheets

(56) References Cited

U.S. PATENT DOCUMENTS

| | | |
|---|---|---|
| 2013/0317333 A1 | 11/2013 | Yang et al. |
| 2014/0156043 A1 | 6/2014 | Blackadar et al. |
| 2014/0180019 A1 | 6/2014 | Martinez et al. |
| 2014/0197531 A1 | 7/2014 | Bolognia |
| 2014/0221797 A1* | 8/2014 | Bailey ............... A61B 5/0002 600/324 |
| 2015/0124566 A1* | 5/2015 | Lake ............... G04G 21/08 368/10 |
| 2015/0277559 A1* | 10/2015 | Vescovi ............... G06F 3/014 345/173 |

* cited by examiner

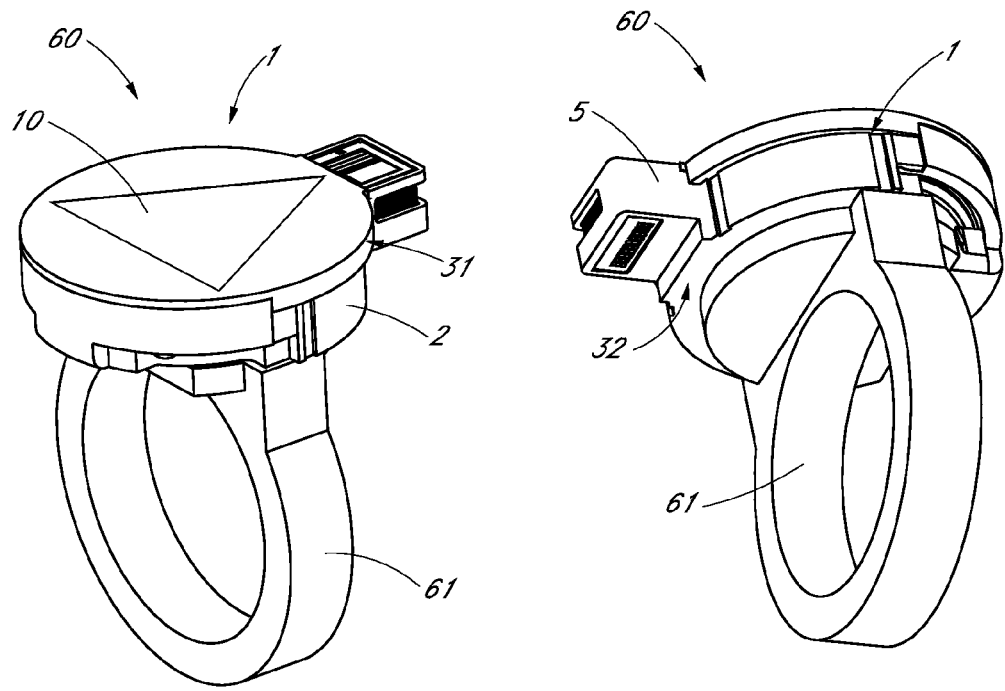
FIG. 6A
FIG. 6B
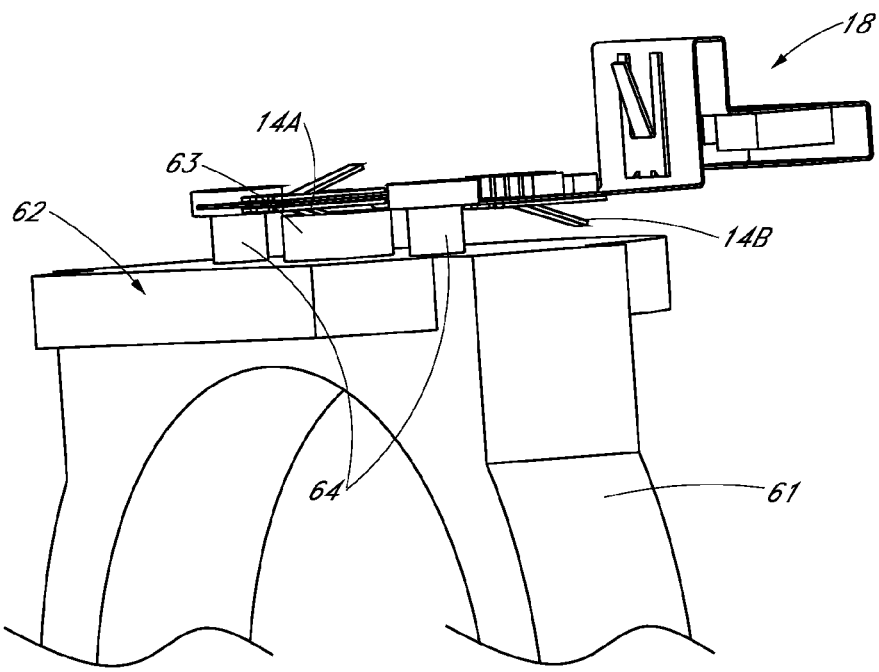
FIG. 6C

COMPACT WEARABLE BIOLOGICAL SENSOR MODULES

BACKGROUND

1. Field of the Invention

The field relates to apparatus and methods for packaging, and in particular, to apparatus and methods for forming compact wearable biological sensor modules.

2. Description of the Related Art

Biological sensors can be used to detect various properties or vital signs of the human body. For example, various biosensors can be used to monitor a user's heart rate, the electrical activity of the heart, blood sugar, blood pressure, blood oxygen content, etc. Many users desire the ability to measure such properties and vital signs on their own, e.g., without going to the clinic to see a physician. Furthermore, many users would like the ability to wear various types of biosensors during their regular day-to-day activities without having the biosensors intrude upon their daily life. Accordingly, there remains a continuing need for improved wearable biosensors.

SUMMARY

In one embodiment, a sensor module is disclosed. The sensor module can include a battery housing comprising a battery cavity sized and shaped to receive a battery. The battery cavity can be defined at least in part by a wall configured to be disposed about at least a portion of a periphery of the battery. The sensor module can include a package housing disposed on the wall of the battery housing. The package housing can be smaller than the battery housing and comprising a package cavity. The sensor module can comprise an integrated device package disposed in or coupled with the package cavity, the integrated device package comprising one or more integrated device dies. The sensor module can include an interfacing feature coupled with the battery housing and extending transverse to the wall. The interfacing feature can be configured to transduce a biological signature into a signal to be processed by the integrated device package. The sensor module can also include an interconnect assembly that electrically connects the interfacing feature to the integrated device package.

In another embodiment, a method of manufacturing a compact sensor module is disclosed. The method can include providing a battery housing comprising a battery cavity defined at least in part by a wall. The method can also include providing a package housing disposed on the wall, the package housing smaller than the battery housing and comprising a package cavity. The method can include connecting an integrated device package to an interconnect assembly, the integrated device package comprising one or more integrated device dies. The method can include disposing the integrated device package in the package cavity. The method can include coupling an interfacing feature with the battery housing, the interfacing feature extending transverse to the wall and configured to transduce a biological signature into a signal to be processed by the integrated device package. The method can also include electrically connecting the interfacing feature to the interconnect assembly.

In yet another embodiment, a sensor module is disclosed. The sensor module can include a battery housing sized and shaped to receive and support one or more batteries. The sensor module can comprise a substrate comprising a first portion coupled with a wall of the battery housing and a second portion extending outwardly from the first portion. The sensor module can include an interfacing feature disposed on a bottom side of the second portion of the substrate and configured to transduce a biological signature of a user to an electrical signal. The sensor module can include one or more integrated device dies mounted to the first portion of the substrate and configured to process the electrical signal.

In yet another embodiment, a sensor module is disclosed. The sensor module can include one or more housings sized and shaped to receive a battery. The sensor module can include an integrated device package disposed in or coupled with the one or more housings. The sensor module can include an interfacing feature exposed on an exterior surface of the one or more housings and configured to transduce a biological signature into a signal to be processed by the integrated device package. The integrated device package can comprise a processor configured to analyze the signal and a wireless communications die configured to provide wireless communication with an external device. The sensor module can be sized and shaped to have a volume less than about 3300 cubic millimeters.

In another embodiment, a sensor module is disclosed. The sensor module can include one or more housings sized and shaped to receive a battery having a battery volume $V_B$. The sensor module can include an integrated device package disposed in or coupled with the one or more housings. The sensor module can include an interfacing feature exposed on an exterior surface of the one or more housings and configured to transduce a biological signature into a signal to be processed by the integrated device package. The integrated device package can comprise a processor configured to analyze the signal and a wireless communications die configured to provide wireless communication with an external device. The sensor module can have a module volume $V_M$ that is larger than the battery volume $V_B$ by a factor K such that $V_M = K * V_B$, wherein the factor K is in a range of about 1.1 to about 3.5.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These aspects and others will be apparent from the following description of preferred embodiments and the accompanying drawing, which is meant to illustrate and not to limit the invention, wherein:

FIG. 6A is a top, left, rear perspective view of a ring that incorporates the sensor module of FIGS. 1A-2.

FIG. 6B is a bottom, right, front perspective view of the ring of FIG. 6A.

FIG. 6C is a perspective view of a ring body electrically connected to the interconnect assembly shown in FIG. 4, with the sensor module housing omitted.

DETAILED DESCRIPTION

Figure 1A:
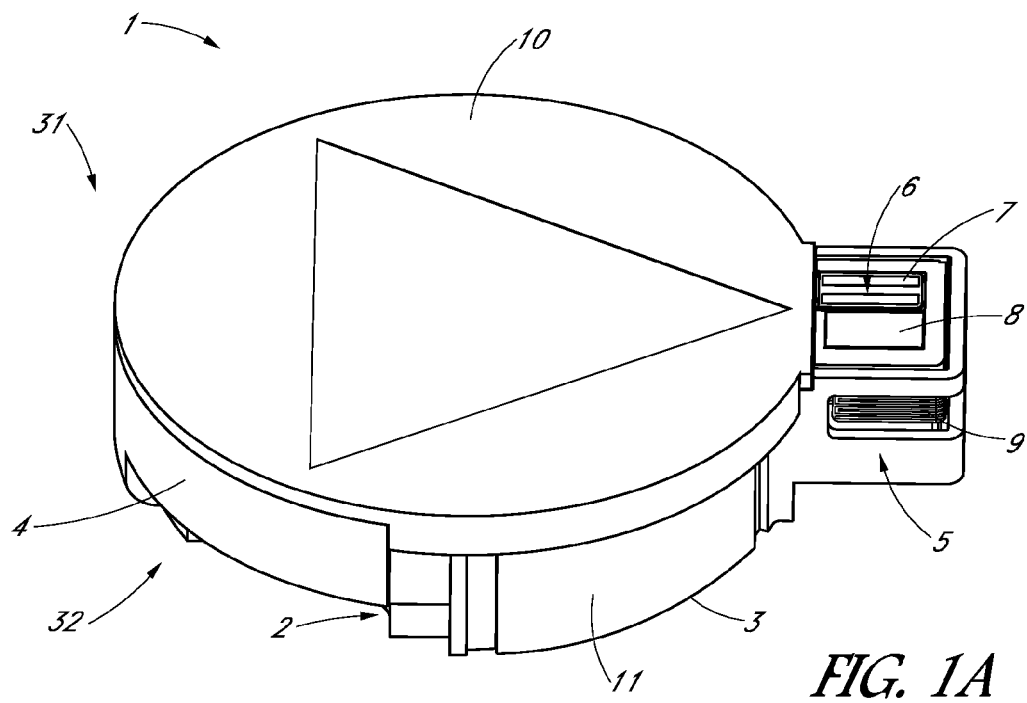
FIG. 1A is a top, left side perspective view of a sensor module, according to various embodiments.

Various embodiments disclosed herein relate to wearable biological sensor modules that can measure various properties or vital signs of the user while the user is wearing the sensor module during his or her regular activities. For example, the sensor modules disclosed herein can be integrated into any suitable wearable apparatus, such as a ring to be worn on the user's finger, an earring, a wristband, a patch or bandage to be adhered to the user's body, or any other suitable type of apparatus. The sensor modules disclosed herein can measure any suitable biological signature (e.g., biological property, characteristic, or vital sign), such as heart rate, heart cycle, heart electrical activity or profile (e.g., an electrocardiogram device, or ECG device), blood sugar, blood pressure, blood oxygen content, number and rate of footsteps etc. In some embodiments, the sensor module can measure multiple biological signatures simultaneously. In some embodiments, the sensor module can comprise a plurality of operating modes, each operating mode configured to measure one or more biological signatures.

The sensor module can provide multiple functions for the user. For example, the sensor module can have various interfacing features with which the user (or the user's computing device) can interact or interface. The interfacing features can be configured to receive an input from the user and/or to transduce a biological signature into a signal to be processed by an integrated device package. One type of interfacing feature is an electrode configured to detect electrical impulses from the user's body. In some embodiments, multiple electrodes can be used in an ECG device to track the changes in voltage between two electrodes coupled with the user's body, which can in turn be processed to track the user's heart rate and/or electrical activity of the heart. Another type of interfacing feature is an optical sensor that can include an optical receiver and/or transmitter (e.g., light emitting diode, or LED). The optical sensor can be configured to measure heart rate, blood oxygen level (e.g., using pulse oximetry), etc., by way of light transmitted through or reflected by the anatomy. Still another example of an interfacing feature is a capacitive touch sensor configured to detect touch input commands from the user. In some embodiments, an interfacing feature can comprise an antenna that transmits wireless signals from the sensor module to another computing device (or receives wireless signals from another computing device), such as a mobile smartphone, laptop computer, tablet computer, etc.

Advantageously, the sensor module can be provided in a compact volume so as to be easily wearable by the user without interfering with the user's day-to-day activities. It should be appreciated that, in some arrangements, the size of the battery may define the minimum size of the overall sensor module or assembly. The batteries used to provide power to a wearable sensor device may be large relative to the individual components of the remainder of the system. For example, the size of the battery may be significantly larger than the interfacing feature (e.g., electrode, wireless sensor, etc.) or a particular integrated device die (e.g., a processor die). In various embodiments disclosed herein, the size of the sensor module can be scaled so as to be only slightly larger than the battery, e.g., a battery-scale module or package. For example, the sensor module can include a battery housing comprising a battery cavity sized and shaped to receive a battery. The battery cavity can be defined at least in part by a wall disposed about at least a portion of a periphery of the battery. A cover can be disposed over the battery cavity to define a top side of the battery housing. A platform can be coupled to or formed with an end of the wall to define a bottom side of the battery housing. The battery, which may comprise a coin-type battery cell, may be disposed in the battery cavity.

The sensor module can include a package housing disposed on the wall of the battery housing on a side of the wall opposite the battery cavity. The package housing can be smaller than the battery housing and can include or define a package cavity. An integrated device package can be disposed in the package cavity. The integrated device package can comprise one or more integrated device dies, such as processor dies, wireless communication dies, motion sensor dies, microphone device dies, pressure sensor dies, and any other suitable type of device die. An interfacing feature (such as an electrode, an optical sensor, etc.) can be coupled with the battery housing and can extend transverse to the wall. In some embodiments, the interfacing feature can be coupled to or formed with the cover over the battery cavity on the top side of the battery housing. For example, in some arrangements, the interfacing feature can be integrated with or formed from a flexible substrate. As an example, the interfacing feature can be patterned in the flexible substrate. In some embodiments, the interfacing feature (or a second interfacing feature) can be coupled to the platform on the bottom side of the battery housing. The interfacing feature can be configured to transduce a biological signature into a signal to be processed by the integrated device package. For example, in some embodiments, the interfacing feature can comprise an electrode that transduces electrical impulses from the user's body into a signal to be analyzed by a processor die in the integrated device package. In some embodiments, the interfacing feature can comprise an optical sensor that transduces optical signatures representative of blood oxygen into an electrical signal to be analyzed by a processor die. A substrate can electrically connect the interfacing feature to the integrated device package. In some embodiments, analog-to-digital converter dies may be disposed near the interfacing features to convert the transduced analog signal into a digital signal to be processed by a sensor die. Positioning the analog-to-digital converter near the interfacing feature can advantageously reduce signal degradation before the signal is digitized, as compared with systems in which the analog-to-digital converter is disposed remote from the interfacing feature.

Thus, the embodiments disclosed herein can provide a multi-functional, compact biological sensor module. The use of multiple types of interfacing features can enable the user to have a rich experience with the sensor module. For example, the user can switch the device on or off, or can switch modes, by swiping or tapping a capacitive touch sensor with his or her finger. One or more electrodes can be used to monitor the user's cardiac activity. An optical sensor can be used to monitor the user's cardiac activity, blood oxygen content, etc. A motion sensor die (e.g., accelerometer, gyroscope, etc.) in the integrated device package can detect user movements to monitor user's footsteps or velocity, and/or to detect whether or not to activate the sensor module based on whether the user is moving. For example, the motion sensor die can be configured to activate the module when the user begins to move and/or to deactivate the module, or put it into sleep mode, when the user has ceased moving for a period of time. An antenna can be used to communicate data regarding the user's biological signatures to the user's computing device (such as a mobile smartphone, laptop computer, tablet computer, desktop computer, mobile computing eyewear, etc.) or to a central server so that the user can view and/or store the data.

To enable the multi-functionality of the sensor modules disclosed herein, multiple different integrated device dies may be used and incorporated into the package. For example, the integrated device package can include a first device die to process the biological signatures detected by the electrode (e.g., for an ECG or heart rate monitor), a second device die to process wireless communications, a third die to process the capacitive sensor signals, a fourth die for sensing user motion, a fifth die to process the signals from the optical sensor, a sixth die to control the operation of the sensor module, and various other dies or passive components to perform other functions performed by the module.

The use of numerous device dies may complicate inter-die and inter-device electrical communications and may occupy valuable real estate within the sensor module. Advantageously, the embodiments disclosed herein can integrate numerous device dies and passive electronic components into a small volume while maintaining appropriate signal chains between the dies and between the package and other external devices. For example, in various embodiments, the device dies can be mounted to a package substrate (e.g., a flexible substrate) that is wrapped or folded multiple times about a carrier. The carrier can support the package substrate and device dies. Some integrated device dies may be disposed inside the volume of the carrier while other device dies (e.g., those that include interfacing features) may be exposed on the package exterior. By wrapping or folding the substrate, the embodiments disclosed herein can form a compact device package that utilizes three spatial dimensions for arranging the device dies and maintaining electrical communication. Each embodiment disclosed herein can incorporate the compact integrated device packages disclosed in U.S. Patent Publication No. US 2014/0197531, filed on Jan. 11, 2013, the contents of which are incorporated by reference herein in their entirety and for all purposes. For example, the device package 100 shown in FIGS. 1B, 1D, 1F, and 1H-1J, or the device package 1 shown in FIGS. 3A-3B of US 2014/0197531 can be adapted for employment in the embodiments described herein.

Figure 1B:
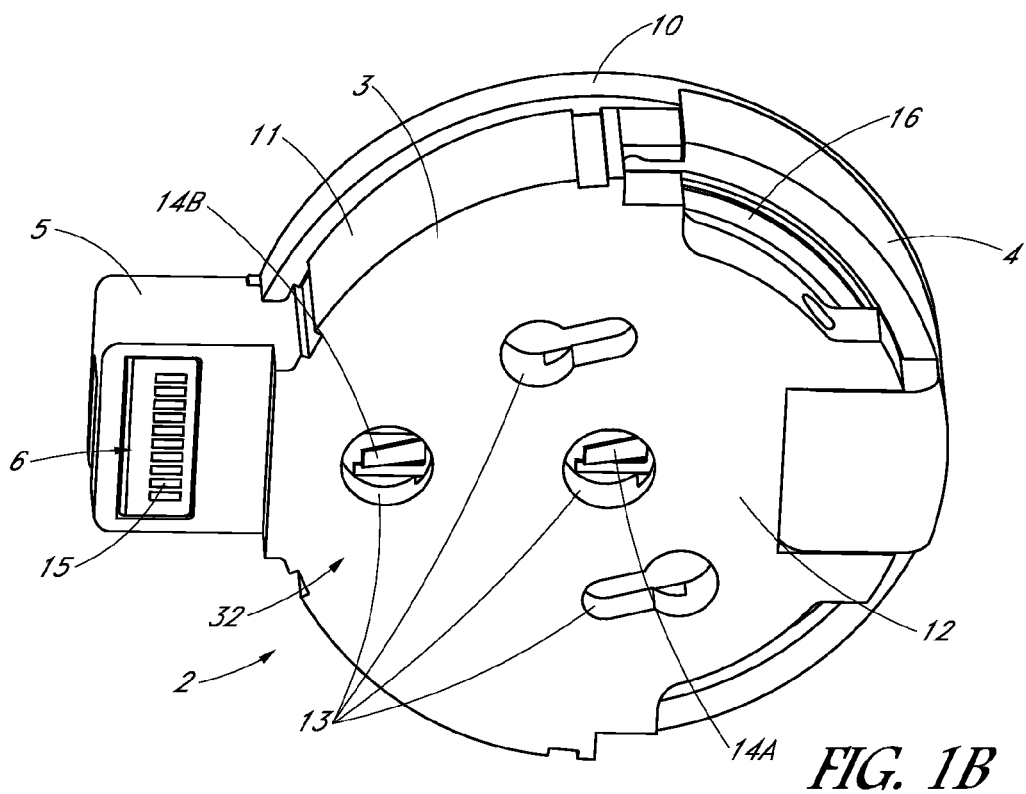
FIG. 1B is a bottom, right side perspective view of the sensor module of FIG. 1A.

FIG. 1A is a top, left side perspective view of a sensor module 1, according to various embodiments. FIG. 1B is a bottom, right side perspective view of the sensor module 1 of FIG. 1A. The sensor module 1 can include a battery housing 2 sized and shaped to receive or support a battery 16. The battery housing 2 can include a housing body 3 and a door 4 operably engaged with the housing body 3. The door 4 can be removed or pivoted relative to the housing body 3 to allow the battery 16 to be inserted into or removed from the battery housing 2. The battery housing 2 can comprise a wall 11 that extends about at least a portion of a periphery of the battery 16. For example, the wall 11 can be curved to define a semi-circular profile that generally conforms to the shape and size of the battery 16. The battery housing 2 can also include a platform 12 coupled to or formed with an end of the wall 11 to form or define a bottom side 32 of the battery housing 2. The platform 12 and wall 11 can cooperate to support and/or protect the battery 16. A cover 10 can couple with the wall 11 to define a top side 31 of the battery housing 2. In some embodiments, the cover 10 can comprise an interfacing feature, such as an electrode. In other embodiments, the cover 10 may be electrically inactive.

The sensor module 1 can also include a package housing 5 and an integrated device package 6 disposed in or coupled with the package housing 5. As shown in FIGS. 1A-1B, the package housing 5 can be disposed on the wall 11 of the battery housing 2. The wall 11 of the battery housing 2 can be disposed between the battery 16 and the integrated device package 6 such that the package 6 is disposed on a side of the wall 11 opposite the battery 16. In other embodiments, the wall 11 may not be disposed to intervene between the package housing 5 and the battery 16. Rather, the package housing 5 may be coupled to or formed with the wall 11, and there may be an opening or pathway between the wall 11 and package 6. In the illustrated embodiment, the platform 12, wall 11, and package housing 5 are integrally formed to define a unitary body, e.g., a single unit. In other embodiments, the platform 12, wall 11, and package housing 5 can comprise separate units that are mechanically connected together. The overall size and footprint of the sensor module 1 can be reduced by integrating the battery 16, battery housing 2, package housing 5, and package 6 into a small compact space. For example, disposing the package housing 5 on the wall 11 of the battery housing 2 and providing the package 6 within the package housing 5 can enable a sensor module 1 having a small volume.

In some embodiments, the overall size of the sensor module 1 can be in a range of about 1500 cubic millimeters to about 3300 cubic millimeters, or more particularly in a range of about 2000 cubic millimeters to about 3000 cubic millimeters. For example, the sensor module can have a length in a range of about 20 mm to about 30 mm, a width in a range of about 20 mm to about 30 mm, and a thickness in a range of about 3 mm to about 8 mm. In some embodiments, the size of the package housing 5 can be in a range of about 65 cubic millimeters to about 85 cubic millimeters. For example, the package housing 5 can have a length in a range of about 4 mm to about 8 mm, a width in a range of about 3 mm to about 7 mm, and a thickness in a range of about 1 mm to about 4 mm.

In the disclosed embodiments, the overall size of the sensor module 1 can be only slightly larger than the size of the battery 16 used in the sensor module 1. For example, in some embodiments, the overall size of the sensor module 1 can have a module volume $V_M$ that is larger than a volume of the battery, $V_B$, by a factor K. The module volume $V_M$ can be related to the battery volume $V_B$ by the relationship $V_M = K*V_B$. The factor K can be in a range of about 1.1 to about 3.5 in some embodiments, or more particularly, in a range of about 1.25 to about 3.5 in some embodiments, e.g., in a range of about 1.5 to about 3. In some embodiments, the factor K can be in a range of about 2 to about 3 in some embodiments, or, more particularly, in a range of about 2 to about 2.75 in some embodiments.

As one example, the battery 16 can comprise a 2032 coin cell battery in various arrangements. The 2032 coin cell battery 16 can have a volume of about 1000 cubic millimeters, while the overall volume of the corresponding sensor module 1 can be less than about 3000 cubic millimeters. In this example, therefore, the factor K can be less than about 3. Although this example relates to a 2032 coin cell battery, it should be appreciated that any other suitable type of battery may be used in the sensor module 1. For example, other types of batteries that may be suitable include a zinc air (A675) battery or any other type of battery. In various embodiments, the battery selection can be dependent upon the use life, peak current, peak voltage, and/or size constraints. Additional power management chips may be provided to condition the power. For instance, in various embodiments, the use of light emitting diodes (LEDs) may drive the need for higher voltage and current surges. Further, broadcasting over Bluetooth or radio networks may also cause higher peak currents. In the disclosed embodiments, the 2032 coin cell battery can be stepped up to about 5 V for use with a green LED. In other embodiments, two zinc air batteries can be used in series to provide longer duty cycles. In some embodiments, the light from the LED(s) and/or the wireless signal(s) can be pulsed. Capacitors may also be included to reduce the demand at peak.

The package 6 can include several interfacing features, such as a capacitive touch sensor 7, an optical sensor 8, and a microstrip antenna 9. The interfacing features can be disposed on exterior surfaces of the package 6 and can be exposed by way of one or more windows in the package housing 5. As explained above, the capacitive touch sensor 7 can receive a touch input from the user, for example, to turn the module 1 on or off, or to change modes. The optical sensor 8 can be used to detect user inputs as well, and/or can be used to detect a biological signature such as heart rate, blood oxygen level, etc. The antenna 9 can be configured to transmit and/or receive wireless communications signals to and/or from an external computing device, such as a mobile smartphone, tablet computing device, laptop or desktop computer, etc. For example, after processing the user's heart rate, a communications device die can be configured to transmit information about the heart rate to the user's smartphone by way of the antenna 9. The user can activate an application on the smartphone to view and/or log his or her heart rate (or other biological signature).

With reference to FIG. 1B, the platform 12 of the battery housing 2 can include one or more apertures 13 formed therethrough. The apertures 13 can permit mechanical engagement with an external mounting structure, such as a ring, earring, wristband, patch, or any other suitable apparatus. In addition, the apertures 13 can enable electrical connection between an external mounting structure (such as another interfacing feature) and an interconnect assembly that communicates with the device package 6 (see, e.g., FIG. 4). For example, as shown in FIG. 1B, a first electrical contact 14A and a second electrical contact 14B can be disposed adjacent and/or partially within corresponding apertures 13. The contacts 14A, 14B shown in FIG. 1B can comprise metallic springs that can be compressed when an electrical connector of the external structure is disposed through the apertures 13 and presses against the contacts 14A, 14B. As explained herein, electrodes of an ECG device can electrically couple with the contacts 14A, 14B. For example, an electrode coupled with one arm can electrically connect to the first contact 14A, and an electrode coupled with a leg can electrically connect to the second contact 14B. The cover 10 can comprise an electrode to be coupled with the other arm.

Moreover, as shown in FIG. 1B, one or more electrical leads 15 can be exposed through a window or aperture of the package housing 5. The leads 15 can electrically couple to an external device, such as a docking station or a computing device. In some embodiments, for example, a docking station (not shown) can be provided to store and/or charge the module 1 (e.g., if the battery 16 is rechargeable), or to test various functions of the module 1. The docking station can be used to program and/or configure the sensor module 1, and/or can be used as a bypass power source for the module 1. The docking station can also electrically communicate with the module to receive data from or transmit data to the module 1. In some embodiments, the docking station can include an interfacing feature (such as an electrode) and can be used in conjunction with interfacing features (e.g., one or more electrodes) on the sensor module 1 to measure various biological signatures for the user, for example, as an ECG or heart monitor device.

Figure 2:
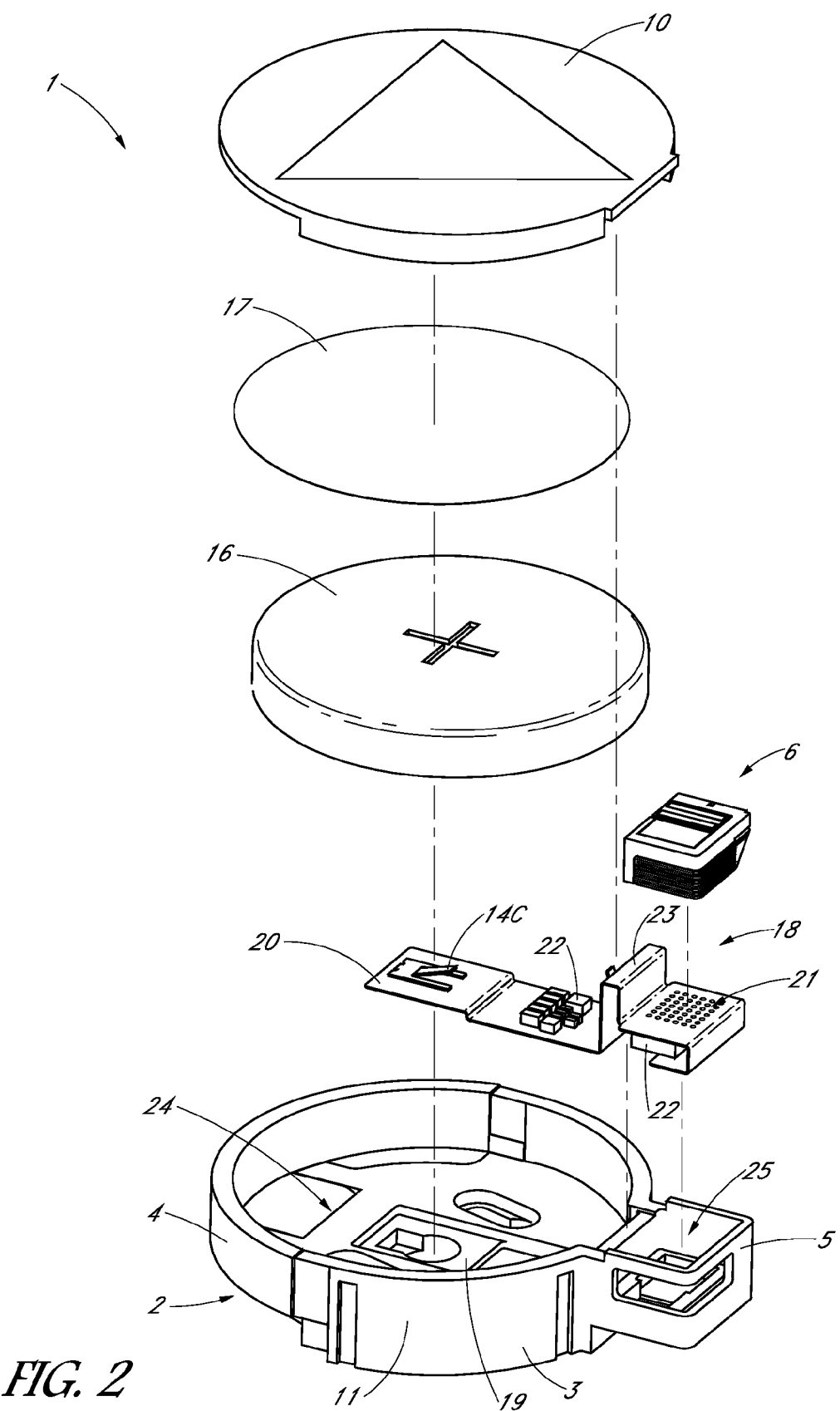
FIG. 2 is a perspective exploded view of the sensor module shown in FIGS. 1A-1B.

FIG. 2 is a perspective exploded view of the sensor module 1 shown in FIGS. 1A-1B. The sensor module 1 can include the battery housing 2, the package housing 5 (coupled to or formed with the battery housing 2), an interconnect assembly 18 (e.g., a flexible substrate), the integrated device package 6, the battery 16, an insulating film 17, and the cover 10. As shown in FIG. 2, the battery housing can include a battery cavity 24 defined at least in part by the wall 11, the platform 12, and/or the cover 10. The battery cavity 24 can be sized and shaped to receive and support the battery 16. The battery housing 2 can protect the battery 16 from the outside environs and external forces. Although the battery cavity 24 shown in FIG. 2 is substantially enclosed by the wall 11, the platform 12, and the cover 10, in other embodiments, the battery cavity 24 may only include the wall 11 and tabs that extend laterally from opposing ends of the wall 11 to capture the battery 16. Thus, in some embodiments, the battery cavity 24 may comprise a partially enclosed structure or recess that can receive and support the battery 16.

The package housing 5 can include a package cavity 25 sized and shaped to receive and support the integrated device package 6. As shown in FIG. 2, the package cavity 25 (and the package 6) can be disposed on a side of the wall 11 opposite the battery cavity 24 and the battery 16. The package housing 5 can be coupled to or formed with the wall 11 of the battery housing 2. In the illustrated embodiment, the wall 11 can intervene between the battery cavity 24 and the package cavity 25. In other embodiments, the wall 11 may not intervene directly between the cavities 24, 25, or the wall 11 may include an opening or other space between the package 6 and the battery 16. Further, the package cavity 25 may be partially or substantially entirely enclosed by the walls of the package housing 5. In some embodiments, the package cavity 25 may comprise a recess defined by one or more walls or tabs of the package housing 5. In other embodiments, the package 6 can be adhered or coupled with the wall 11 of the battery housing 2.

The interconnect assembly 18 can provide electrical communication between the interfacing features and the integrated device package 6. For example, as explained herein, the cover 10 that defines or is disposed on the top side 31 of the battery housing 2 can comprise an interfacing feature that includes an electrode configured to transduce electrical impulses from the user's body. In some embodiments, an additional or alternative interfacing feature can be disposed on or coupled with the bottom side 32 of the battery housing 2 (see FIGS. 6A-9C), e.g., by way of the first and second electrical contacts 14A, 14B shown in FIG. 1B. The interconnect assembly 18 can comprise a substrate 20, which may comprise a flexible substrate configured to bend or fold to conform to a particular geometry. The substrate 20 can include internal conductive traces that are configured to route electrical signals from one electrical device to another.

In the embodiment of FIG. 2, for example, a raised connecting portion 23 of the substrate 20 can electrically connect with the cover 10 when the cover 10 includes an electrode or other interfacing feature. For example, a conductive epoxy, non-conductive paste (NCP), anisotropic conductive film (ACF), conductive epoxy, solder, or any other suitable electrical connection can be provided between the electrode of the cover 10 and the raised connecting portion 23 of the substrate 20. In some embodiments, a spring-loaded contact or clip (similar to the contacts 14A, 14B) can be used to electrically connect the cover 10 with the substrate 20. A third electrical contact 14C, which may comprise a metallic spring, can electrically connect one terminal of the battery 16 (e.g., the negative terminal) with corresponding traces of the substrate 20. Electrical bond pads 21 can be provided on a segment of the substrate 20 to electrically connect to corresponding bond pads of the integrated device package 6. Various electronic device dies 22 can also be mounted to and electrically connected to the substrate 20.

Figure 3:
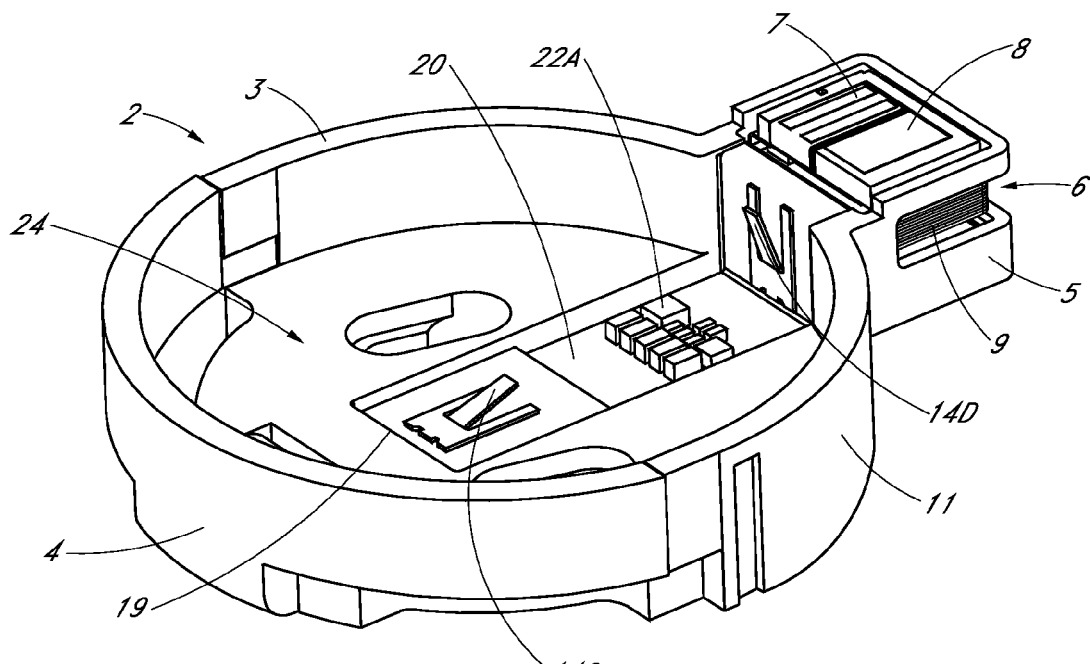
FIG. 3 is a top, left, rear perspective view of an interconnect assembly mounted to a sensor module housing, according to some embodiments.

The integrated device package 6 and the segment of the substrate 20 on which the bond pads 21 are provided can be disposed in the package cavity 25 of the package housing 5. When assembled, as shown in FIG. 3, the substrate 20 can bend upwardly over a neck of the battery housing 2, which can form a portion of the wall 11, and can rest in a recess 19 formed in the platform 12 of the battery housing 5. The battery 16 can rest upon the platform 12, and a terminal of the battery 16 can electrically contact the contact 14C. The insulating film 17 can be disposed above the battery 16 between the battery 16 and the cover 10. The insulating film 17 can electrically separate the cover 10 and the battery 16. The cover 10 (which may include an electrode or other interfacing feature) may mechanically couple to the wall 11 and/or platform 12 of the battery housing 2. For example, the cover 10 may engage with the wall 11 and/or platform 12 by way of a snap-fit connection. The cover 10 and its associated interfacing feature (e.g., electrode) can be disposed transverse to, or in a different direction relative to, the wall 11.

As shown in FIGS. 1A-2, the overall size of the sensor module 1 can be just slightly larger than the battery 16, such that the sensor module 1 can be a compact battery-scale module. For example, when assembled, e.g., in the configuration of FIGS. 1A-1B, the overall size of the sensor module 1 can be in a range of about 1500 cubic millimeters to about 3300 cubic millimeters, or more particularly in a range of about 2000 cubic millimeters to about 3000 cubic millimeters. For example, the sensor module can have a length in a range of about 20 mm to about 30 mm, a width in a range of about 20 mm to about 30 mm, and a thickness in a range of about 3 mm to about 8 mm. In some embodiments, the size of the package housing 5 can be in a range of about 65 cubic millimeters to about 85 cubic millimeters.

Figure 4:
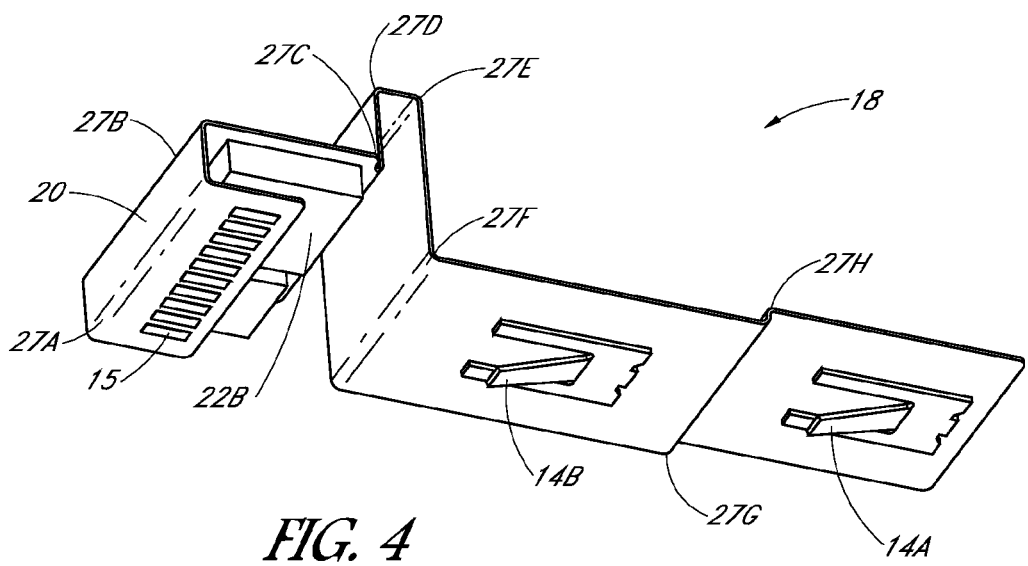
FIG. 4 is a bottom, right, front perspective view of the interconnect assembly shown in FIG. 3.

FIG. 3 is a top, left, rear perspective view of the interconnect assembly 18 and package 6 mounted to the battery housing 2, according to some embodiments. FIG. 4 is a bottom, right, front perspective view of the interconnect assembly 18 shown in FIG. 3. As shown in FIG. 3, the substrate 20 can be at least partially disposed in the recess 19 formed in the platform 12. A plurality of electrical components 22A can be mounted on a segment of the substrate 20 and can be configured to perform power management functions for the battery 16. Further, as shown in FIG. 3, a fourth electrical contact 14D, which may comprise a metallic spring, can connect a second terminal of the battery 16 (e.g., the positive terminal) to corresponding internal traces of the substrate 20. Thus, the third and fourth electrical contacts 14C, 14D can provide an electrical pathway by which the battery 16 can power the sensor module 1. In some arrangements, a power management die can be provided in the package 6 to manage the distribution of electrical power to the module 1.

As shown in FIG. 4, the first and second electrical contacts 14A, 14B can be connected to a bottom side of the substrate 20. As explained above with respect to FIG. 1B, the first and second electrical contacts 14A, 14B can be aligned with corresponding apertures 13 in the housing platform 12 to electrically connect to connectors from an external apparatus, such as an electrode or other interfacing feature of a wristband, ring, earring, patch, bandage, etc. For example, as explained in further detail herein with respect to FIGS. 6A-9C, the connectors of the external apparatus can be inserted into the apertures 13 and can press against the contacts 14A, 14B to electrically couple with the substrate 20, and in turn, to the package 6. The leads 15 are also shown on the substrate 20, and the leads 15 can electrically connect to an external device, such as a docking station, etc. Advantageously, therefore, the sensor module 1 disclosed herein can be used with numerous types of devices, and the external devices can electrically and mechanically connect to the sensor module 1 quickly and easily. In some arrangements, the external device (e.g., wristband, patch, bandage, ring, earring, etc.) can be removably connected with the module 1. Furthermore, as shown in FIG. 4, the substrate 20 can include multiple bends 27A-27H that permit the substrate 20 to conform to the package housing 5 and the battery housing 2. In addition, the device die(s) 22B can be coupled to the substrate 20. The device die(s) 22B can comprise processor dies configured to perform various power management functions related to the battery 16.

Figure 5A:
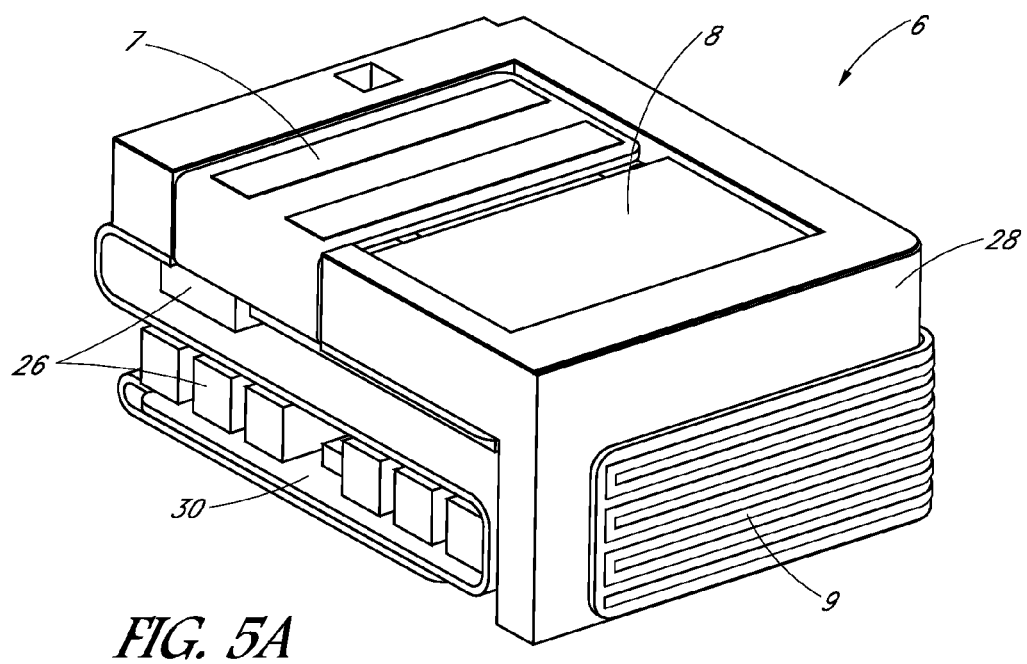
FIG. 5A is a top, left, rear perspective view of an integrated device package used with the sensor module of FIGS. 1A-2.
Figure 5B:
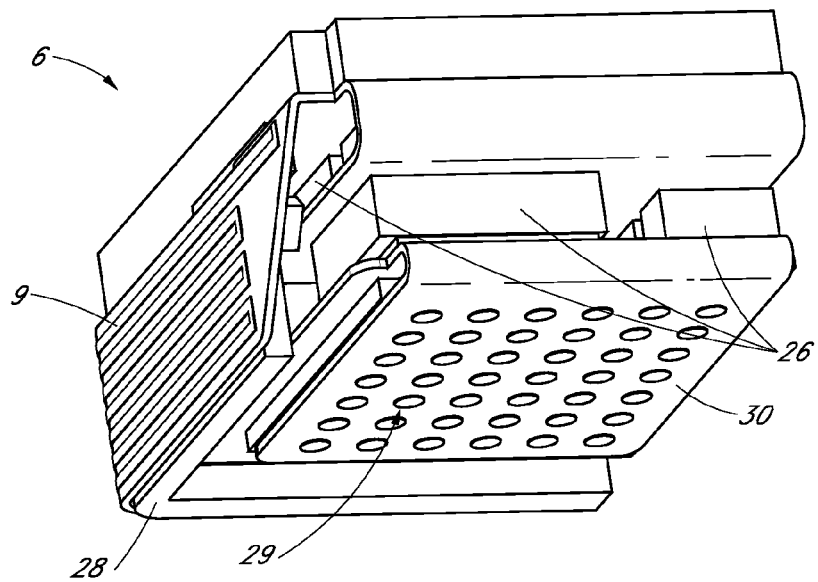
FIG. 5B is a bottom, right, front perspective view of the integrated device package shown in FIG. 5A.

FIG. 5A is a top, left, rear perspective view of an example of the integrated device package 6 used with the sensor module 1 of FIGS. 1A-2. FIG. 5B is a bottom, right, front perspective view of the integrated device package 6 shown in FIG. 5A. As shown in FIGS. 5A-5B, the package 6 can include a package substrate 30 wrapped or folded around a carrier 28. The carrier 28 can comprise a relatively stiff or rigid support structure to which the package substrate 30 can be attached. Multiple integrated device dies 26 and passive devices can be mounted to and electrically connected to the package substrate 30. For example, in the illustrated embodiment, numerous dies 26 can be mounted to both sides of the package substrate 30 and can be distributed throughout the volume of the package 6. The package substrate 30 can include multiple bends within the carrier 28 or housing. Multiple device dies can be disposed on any particular segment between two bends and/or on opposing sides of the segment of the substrate. The multiple bends of the package substrate 30 shown in FIGS. 5A-5B can enable a compact, three-dimensional arrangement of device dies 26 that positions the dies 26 in a relatively small, compact volume and footprint, while at the same time enabling electrical communication among the dies 26 and between the dies 26 and external devices.

Furthermore, the package 6 can comprise one or more interfacing features. Various interfacing features of the package can be disposed transverse to, or along a different direction relative to, the wall 11 of the battery housing 2. For example, the interfacing features can comprise the capacitive touch sensor 7, the optical sensor 8, and/or the antenna 9. The capacitive touch sensor 7 can receive a user touch input to control the operation of the module 1. The optical sensor 8 (which can be transverse to the wall 11) can transmit and/or receive light signals for detecting a user input (e.g., via gesture sensing) and/or a biological signature of the user, such as a heart rate or oxygen level. The antenna 9 can transmit or receive data relating to the processed biological signatures. In various embodiments, the gain of the antenna 9 can be improved by electrically connecting the antenna 9 with the metallic battery 16, such that the metallic battery 16 can extend the range of the data transmitted from or received by the package 6.

As explained above, the device dies 26 can include one or more processor dies to analyze the signals sent from the interfacing features, such as an electrode or optical sensor. The device dies 26 can include other types of devices, such as a motion sensor die, a die to process signals from the optical sensor 8, a die to process signals from the capacitive touch sensor 7, a wireless communications die for processing data transmitted or received by the antenna 9, a controller die for controlling the operation of the module 1, a signal processing die, an integrated passives device die, a microphone or speaker die, and/or any other suitable device dies and/or non-transitory computer-readable storage memories. In addition, one or more bond pads 29 of the package 6 can be configured to electrically connect to corresponding bond pads 21 (FIG. 2) of the interconnect assembly 18. Thus, electrical signals can be sent from the package 6 to the interconnect assembly 18, and vice versa, by way of the bond pads 29, 21. Additional details of the package 6 can be found in U.S. Patent Publication No. US 2014/0197531, filed on Jan. 11, 2013, the contents of which are incorporated by reference herein in their entirety and for all purposes.

FIG. 6A is a top, left, rear perspective view of a ring 60 that incorporates the sensor module 1 of FIGS. 1A-2. FIG. 6B is a bottom, right, front perspective view of the ring 60 of FIG. 6A. FIG. 6C is a perspective view of a ring body 61 electrically connected to the interconnect assembly 18 shown in FIG. 4, with the battery housing 2 omitted for ease of illustration. The ring body 61 can be sized and shaped to be worn on a finger of the user. In some embodiments, the ring body 61 can comprise an interfacing feature, such as a first electrode. For example, the ring body 61 can comprise an annular metallic body configured to transduce electrical impulses from the user's finger to the package 6. In addition, the cover 10 of the sensor module 1 can comprise a second electrode interfacing feature transverse to the wall 11 of the battery housing 2. For example, the cover 10 can be disposed over and generally parallel to the major dimensions of the battery 16.

As shown in FIGS. 6A-6B, the ring body 61 can mechanically couple with the bottom side 32 of the battery housing 2. As shown in FIG. 6C, one or more studs 64 can extend from a support 62 of the ring body 61. With reference to FIG. 1B, for example, the studs 64 can extend through corresponding apertures 13 of the platform 12 of the battery housing 2 to mechanically secure the ring body 61 to the battery housing 2. In some arrangements, the ring body 61 can be removed from the module 1 by the user; in other embodiments, the ring body 61 and module 1 can be configured to be permanently or semi-permanently secured. Further, a connector 63 can extend from the support 62 through a corresponding aperture 13 to electrically connect the ring body 61 with at least one of the first and second electrical contacts 14A, 14B that are mounted to the substrate 20 of the interconnect assembly 18. Further, the electrode of the cover 10 can electrically couple with the substrate in a variety of ways, as explained above.

In use, the user can insert his or her finger through the ring body 61. For purposes of this example, the user can insert a finger of his or her right hand through the ring body 61. The user can activate or power on the system by tapping the capacitive touch sensor 7 or another control mechanism. In some arrangements, the ring 60 can automatically activate when the user moves, based on determinations made by a motion sensor die of the package 6, or by touching the cover 10 with one finger while the ring 60 is on another finger, as described below. In some embodiments, the electrode of the ring body 61 can detect electrical impulses generated by the right arm through the finger. For an ECG or heart rate monitoring device, the user can place a finger from the left hand on the electrode of the cover 10. Thus, a circuit from the electrode on the cover 10 (by way of the finger from the left hand that contacts the cover 10), and to the electrode on the ring body 61 (by way of the finger from the right hand that contacts the ring body 61) is completed through the user's body, such that the sensor module can detect heart-related electrical signals from the user's body. The electrical signals can be transmitted to the associated integrated device die of the package 6 by way of corresponding internal traces of the substrate 20 of the interconnect assembly 18.

The various device dies 26 of the package 6 can process the transduced signals to determine the heart rate or other electrical profile of the user's heart. The communications die of the package 6 can transmit data regarding the heart rate or other activity to the user's mobile device, and the user can view the data on a suitable display, for example, by way of an application on a mobile smartphone or tablet computing device.

Figure 7A:
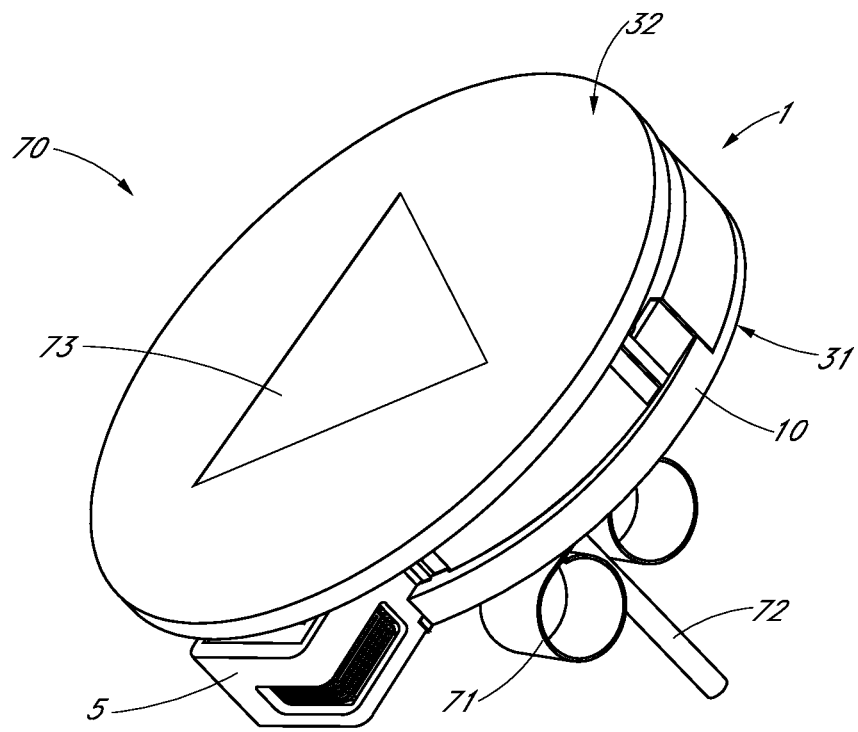
FIG. 7A is a top, right, front perspective view of an earring that incorporates the sensor module of FIGS. 1A-2.
Figure 7B:
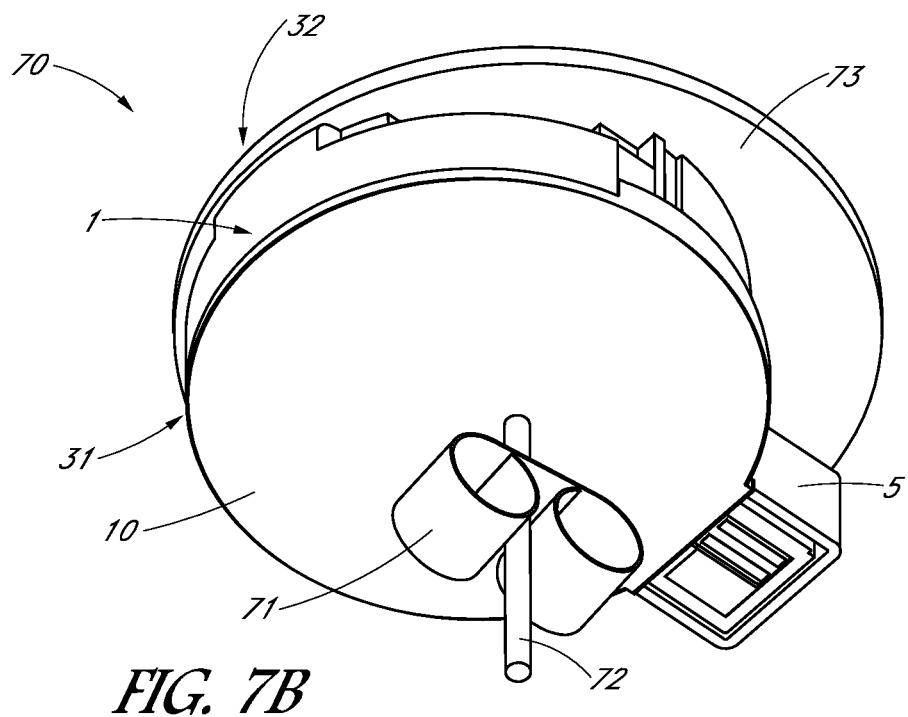
FIG. 7B is a bottom, left, rear perspective view of the earring of FIG. 7A.

FIG. 7A is a top, right, front perspective view of an earring 70 that incorporates the sensor module 1 of FIGS. 1A-2. FIG. 7B is a bottom, left, rear perspective view of the earring 70 of FIG. 7A. The cover 10 of the top side 31 of the module 1 can comprise an interfacing feature including a first electrode in electrical communication with the package 6. The earring 70 can include a connector 71 coupled with a stud 72. The connector 71 can press the user's ear against the first electrode of the cover 10 to enable electrical signatures from the ear to be received by the cover 10. In other embodiments, the interfacing feature of the cover 10 can comprise an optical sensor or other feature which can continuously monitor biological signatures of the user.

Further, a second electrode 73 can be coupled with a bottom side 32 of the battery housing 2 to electrically communicate with the package 6. For example, the second electrode 73 can couple with the interconnect assembly 18 or substrate 20 similar to the arrangement shown with respect to the ring 60 of FIGS. 6A-6C. In some embodiments, the user can press his or her finger against the interfacing feature or second electrode 73. For example, the user can wear the earring 70 on the right ear and can press a finger from her left hand against the second electrode 73. The device dies 26 in the package 6 can process the electrical signals between the first electrode of the cover 10 and the second electrode 73 through the user's body to monitor a heart rate or other cardiac activity of the user, for example, similar to an ECG device.

Figure 8A:
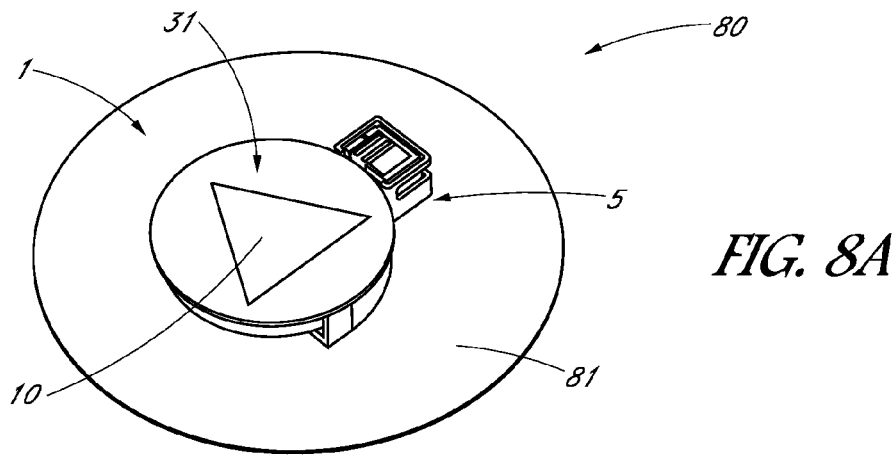
FIG. 8A is a top perspective view of a patch that incorporates the sensor module of FIGS. 1A-2.
Figure 8B:
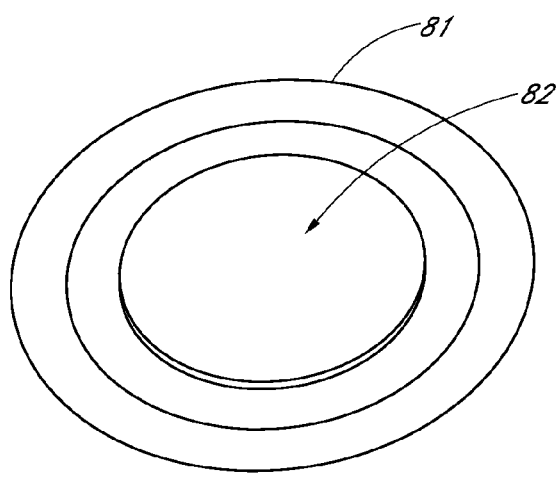
FIG. 8B is a bottom perspective view of the patch shown in FIG. 8A.
Figure 8C:
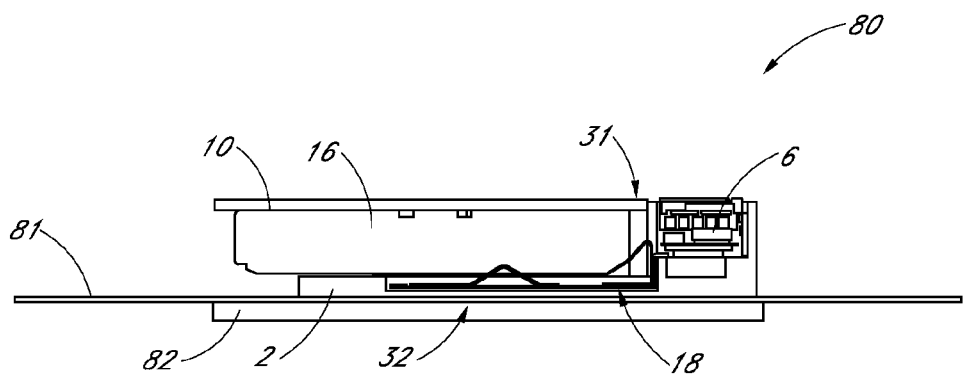
FIG. 8C is a side cross-sectional view of the patch shown in FIGS. 8A-8B.

FIG. 8A is a top perspective view of a patch 80 that incorporates the sensor module 1 of FIGS. 1A-2. FIG. 8B is a bottom perspective view of the patch 80 shown in FIG. 8A. FIG. 8C is a side cross-sectional view of the patch 80 shown in FIGS. 8A-8B. The patch 80 can include an adhesive film 81 coupled with the sensor module 1 between an interfacing feature 82 (e.g., an electrode) and the bottom side 32 of the battery housing 2. The interfacing feature 82 may be transverse to the wall 11 of the battery housing 2, and may extend generally parallel to the battery 16. The patch 80 can be configured such that the interfacing feature 82 is between the adhesive film 81 and the user when the patch 80 is worn by the user. The interfacing feature 82 can electrically couple with the substrate 20 or interconnect assembly 18 in any suitable way, including the arrangements described herein with respect to FIGS. 6A-7B. In the embodiment of FIGS. 8A-8C, the cover 10 of the sensor module 1 may be electrically inert; in other arrangements, the cover 10 can comprise an electrode or other interfacing feature. In such an arrangement, a second patch 80 is attached on another part of the user's body to complete the circuit and enable the patch 80 to monitor the user's heart rate. For example, one patch 80 can electrically communicate with another patch 80 to complete the circuit. In some arrangements, the patch 80 can comprise multiple electrodes that form a complete circuit when connected to the user's body.

In use, the user can adhere one or more patches 80 to his or her skin. If multiple patches 80 are used, the data from the patches 80 can be compiled by the package(s) 6 to define an ECG or heart monitor device. The adhesive film 81 can removably attach the patch 80 to the user. The interfacing feature 82 can transduce one or more biological signatures from the skin to the package 6.

Figure 9A:
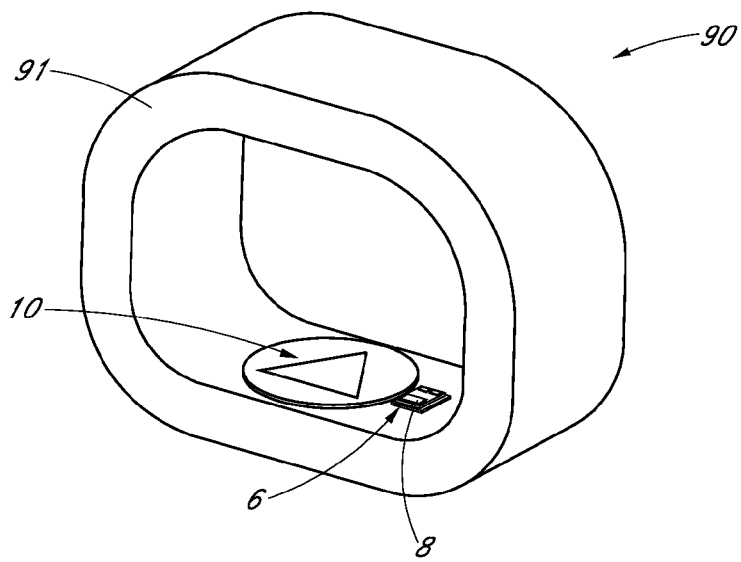
FIG. 9A is a bottom perspective view of a wristband that incorporates the sensor module of FIGS. 1A-2.
Figure 9B:
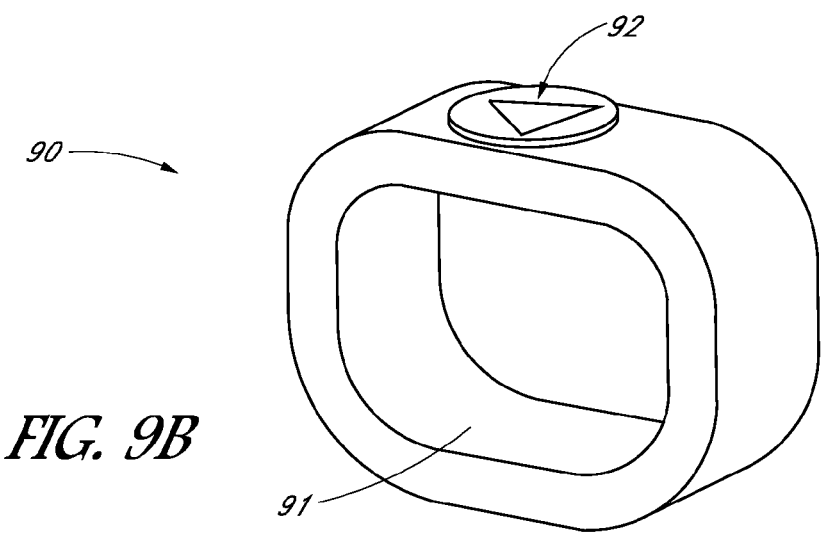
FIG. 9B is a top perspective view of the wristband of FIG. 9A.
Figure 9C:
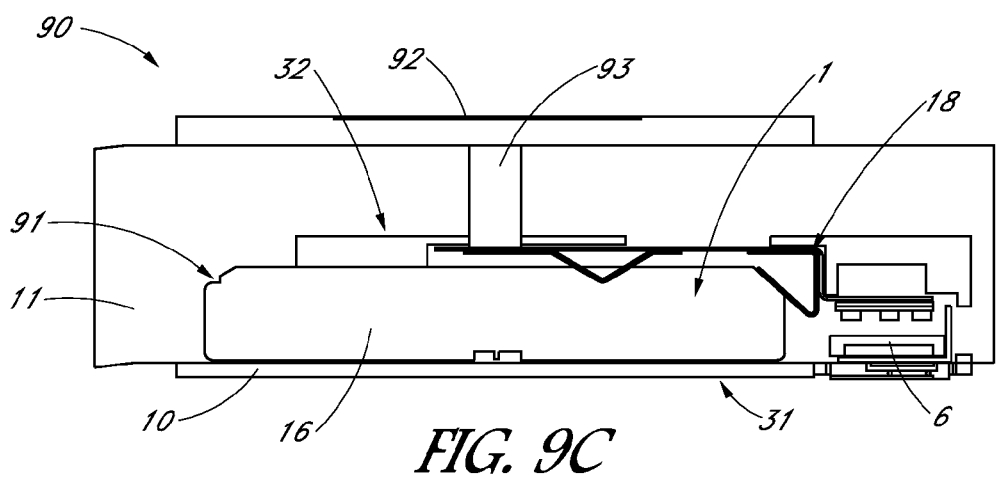
FIG. 9C is a side cross-sectional view of the wristband shown in FIGS. 9A-9B.

FIG. 9A is a bottom perspective view of a wristband 90 that incorporates the sensor module 1 of FIGS. 1A-2. FIG. 9B is a top perspective view of the wristband 90 of FIG. 9A. FIG. 9C is a side cross-sectional view of the portion of the wristband 90 shown in FIGS. 9A-9B that houses the sensor module 1. The wristband 90 can include a wristband body 91 sized and shaped to be worn on a wrist of the user. The sensor module 1 can be mounted to the wristband body 91. Various interfacing features can be exposed through the wristband body 91 on interior and/or exterior surfaces of the wristband body 91. For example, as shown in FIGS. 9A-9B, the sensor module 1 can be arranged such that the cover 10 and optical sensor 8 are exposed on an interior surface of the wristband body 91, such that the cover 10 and optical sensor 8 are respectively in contact with and in proximity of the user's wrist. In various embodiments, the optical sensor 8 of the package 6 (or other interfacing feature on the cover 10) can continuously monitor one or more biological signatures of the user, e.g., heart rate, blood oxygen level, etc. In some embodiments, the cover 10 comprises a first electrode, which can transduce electrical impulses from the user's wrist.

In addition, a second interfacing feature 92 can be disposed on an exterior surface of the wristband body 91 transverse to the wall 11 of the battery housing 2. The second interfacing feature 92 can comprise a second electrode to transduce electrical impulses from the user's body. As shown in FIG. 9C, a connector 93 can electrically connect the second interfacing feature 92 with the interconnect assembly 18 or substrate 20 to provide electrical communication between the interfacing feature 92 and the package 6. For example, the user can wear the wristband 90 on one wrist, and can press a finger from his opposite hand on the second interfacing feature 92 (e.g., a second electrode) to monitor a heart rate or other cardiac signal of the user.

Figure 10:
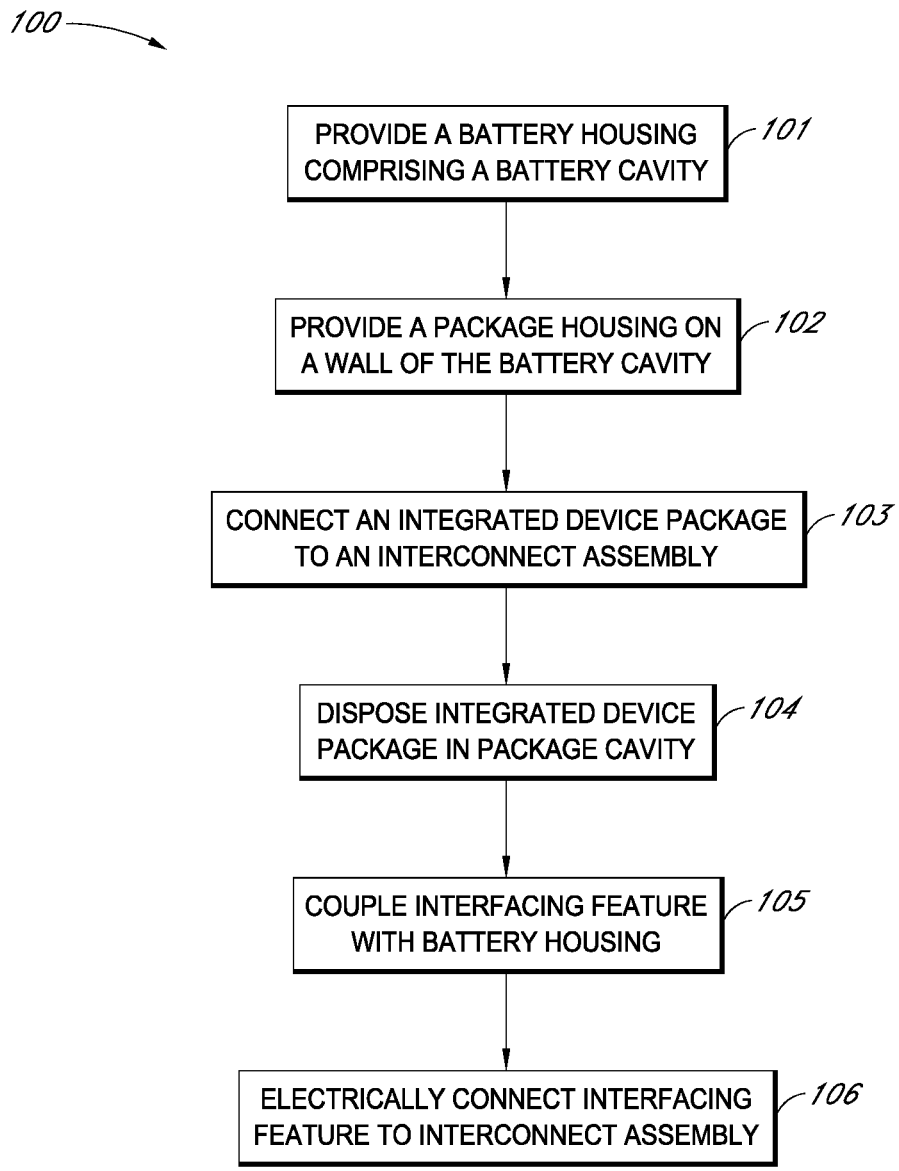
FIG. 10 is a flowchart illustrating a method of manufacturing a compact sensor module, in accordance with some embodiments.

FIG. 10 is a flowchart illustrating a method 100 of manufacturing a compact sensor module, in accordance with some embodiments. In a block 101, a battery housing comprising a battery cavity defined at least in part by a wall is provided. For example, the battery housing can comprise a platform coupled or formed with an end of the wall to define a bottom side of the battery housing. A cover can be disposed over the battery cavity to define a top side of the battery housing. The battery housing can be sized and shaped to receive and support a battery, such as a disc- or coin-shaped battery. In some embodiments, a door can be provided to permit the battery to be inserted and removed from the battery housing.

Turning to a block 102, a package housing can be provided. The package housing can be disposed on the wall of the battery housing. The package housing can be smaller than the battery housing and can include a package cavity. In various arrangements, the package housing and the battery housing can comprise a unitary or integrated structure. In other arrangements, the package housing and the battery housing can comprise separate components that are mechanically connected together. In various embodiments, the wall of the battery housing can separate the battery cavity from the package cavity.

In a block 103, an integrated device package can be connected to an interconnect assembly, which can include a flexible substrate. The integrated device package can include one or more integrated device dies. For example, as explained above, the package can include device dies to process biological signatures detected by the various interfacing features, in addition to other types of device dies. Turning to a block 104, the integrated device package can be disposed in the package cavity.

Moving to a block 105, an interfacing feature can be coupled with the battery housing. The interfacing feature can extend transverse to the wall of the battery housing and can be configured to transduce a biological signature into a signal to be processed by the integrated device package. For example, the interfacing feature can comprise an electrode in some embodiments. In other embodiments, the interfacing feature can comprise an optical sensor. In a block 106, the interfacing feature can be electrically connected to the interconnect assembly, e.g., substrate. The interconnect assembly can thereby provide electrical communication between the interfacing feature and the package. In some arrangements, blocks 104 and 106 can take place simultaneously. For example, portions of the interconnect assembly connected to the integrated device package can be disposed in the package cavity, while portions of the interconnect assembly are disposed in the battery cavity. The package can process the signatures detected by the interfacing features, and can transmit the processed data to an external computing device, such as the user's smartphone or tablet computer for display or storing by the user.

Figure 11:
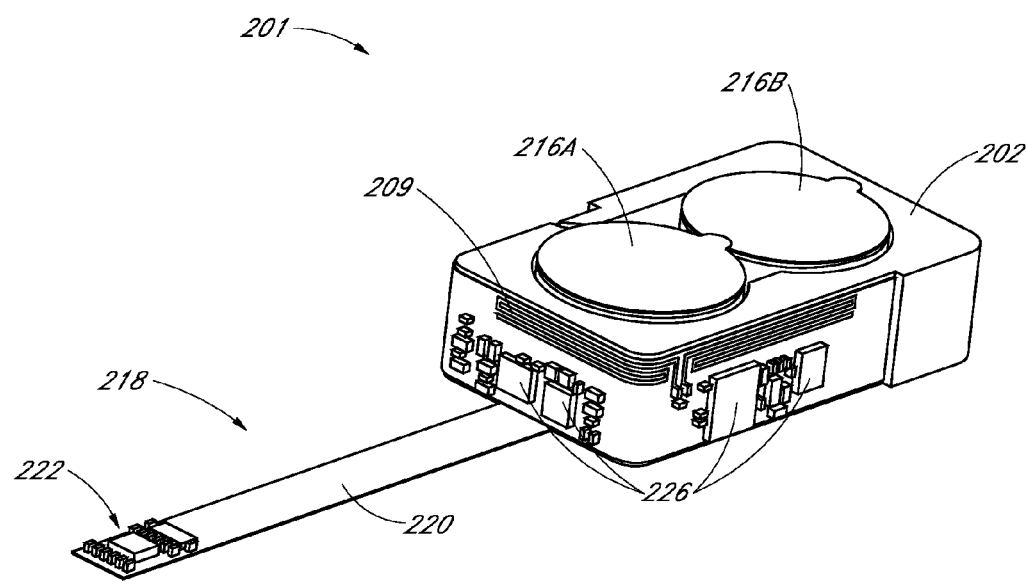
FIG. 11 is a perspective view of a sensor module, according to another embodiment.
Figure 12:
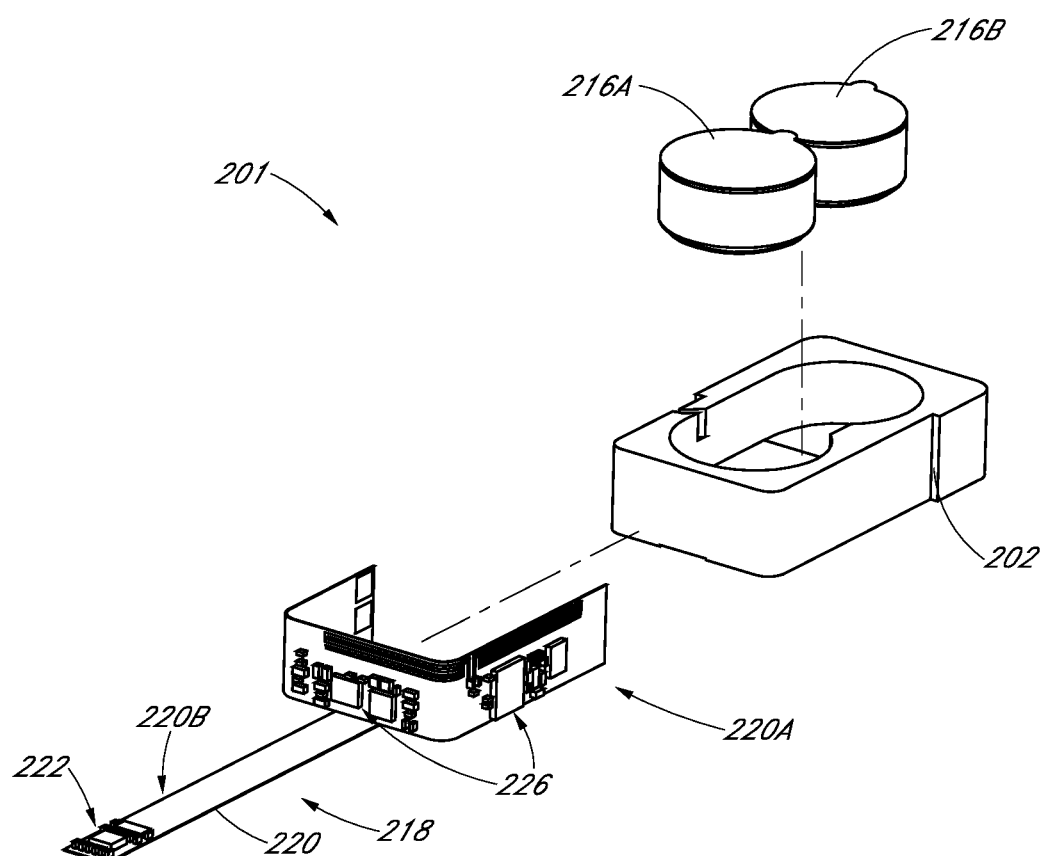
FIG. 12 is a perspective exploded view of the sensor module shown in FIG. 11.
Figure 13:
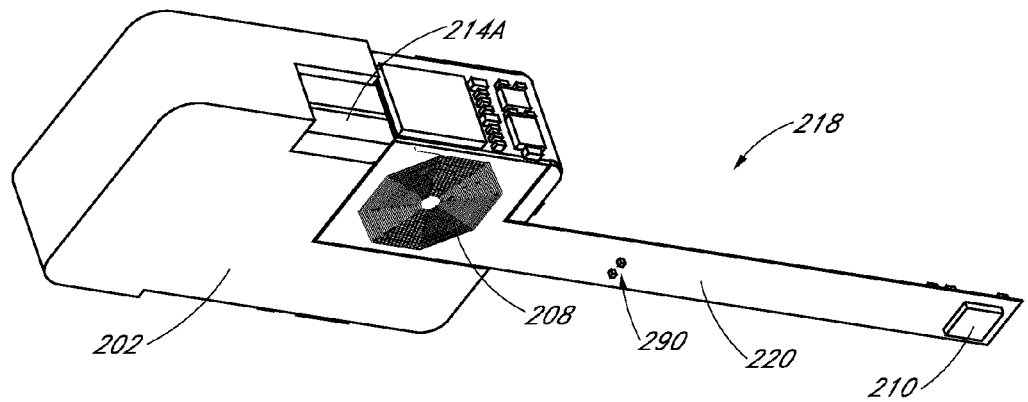
FIG. 13 is a bottom perspective view of the battery housing and interconnect assembly shown in FIG. 11.

FIG. 11 is a top perspective view of a sensor module 201 comprising an interconnect assembly 218 and battery housing 202, according to another embodiment. In various embodiments, the sensor module 201 can be attached to a user's body by way of an attachment mechanism, such as a bandage or tape. In some embodiments, the sensor module can be attached or wrapped around a user's finger to measure various biological characteristics, such as blood oxygen content. FIG. 12 is a perspective exploded view of the sensor module 201 shown in FIG. 11. FIG. 13 is a bottom perspective view of the battery housing 202 and interconnect assembly 218 shown in FIG. 11. The battery housing 202 can be sized and shaped to receive and support a first battery 216A and a second battery 216B. The batteries 216A, 216B can be used to supply power to the sensor module 201. The batteries 216A, 216B can comprise any suitable type of battery, including a tubular or cylindrical shaped battery. For example, the batteries 216A, 216B can comprise two zinc air batteries (e.g., A675 batteries) connected in series to provide a longer duty cycle.

The interconnect assembly 218 can comprise a substrate 220. The substrate 220 can comprise a first portion 220A configured to couple with or fold about the battery housing 202. The substrate 220 can also include a second portion 220B that extends from the first portion 220A. In some embodiments, the first and second portions 220A, 220B can be part of a single substrate; in other embodiments, the first and second portions 220A, 220B can comprise separate substrates. In the illustrated embodiment, the substrate 220 comprises a flexible substrate configured to wrap or fold to conform to a particular shape or structure. As shown in FIG. 13, an interfacing feature 210 can be provided to transduce a biological signature (e.g., heart rate, blood oxygen level, etc.) into a signal to be processed by a suitable processor.

As shown in FIGS. 11 and 12, the first portion 220A can wrap about at least a portion of the battery housing 202, e.g., about one or more walls of the housing 202. One or more integrated device dies 226 can be mounted to and electrically coupled with the first portion 220A. The device dies 226 can comprise any suitable device die. For example, the device dies 226 can include, e.g., device dies to process signals transduced by various interfacing features (such as an electrode, optical sensor, capacitive touch sensor, antenna, etc.), a power management die, a communications die, a controller die, a signal processing die, and any other number or type of integrated device dies.

Further, with respect to FIGS. 11-13, the second portion 220B can extend from the first portion 220A along a length of the sensor module 201. As shown in FIG. 13, a first interfacing feature 210 can be disposed on a bottom side of the substrate 220 such that the first interfacing feature 210 is exposed through a bottom side of the sensor module 201. The first interfacing feature 210 can comprise an optical sensor, an electrode, or any other suitable interfacing feature configured to transduce a biological signature into an electrical signal. The first interfacing feature 210 can face the user's skin or anatomy when the sensor module 201 is attached to the user (e.g., to the user's finger by way of a suitable attachment mechanism). For example, the interfacing feature 210 can comprise an optical sensor (such as a photodiode array, or PDA) configured to transduce optical signatures of blood flowing through the user. In such embodiments, one or more light sources 290 (such as light emitting diodes, or LEDs) can be coupled with the substrate 220. During use, the second portion 220B can be wrapped around the user's finger such that the finger is disposed between the light source(s) 290 (e.g., LEDs) and the first interfacing feature 210 (e.g., a PDA). Light emitted from the light source(s) 290 can pass through the user's finger and can be received by the first interfacing feature 210. The sensor module 1 can process the signals received or transduced by the first interfacing feature 210 to measure the user's blood oxygen content in various embodiments.

One or more processing dies 222 (and/or passive devices) can be coupled with a top side of the first portion 220A. The one or more processing dies 222 can smooth out the signals before transmission to the device dies 226. The electrical signal from the first interfacing feature 210 can pass along the second portion 220B to the first portion 220A and the device dies 226, which can be configured to process the electrical signals. In some embodiments, the dies 222 can be used to perform power management functions related to the batteries. Suitable device dies 226 on the first portion 220A (e.g., an optical sensor die) can be configured to process the signals to detect an amount of oxygen in the user's blood.

In addition, as shown in FIGS. 11 and 13, a second interfacing feature 208 and a third interfacing feature 209 can be disposed on the first portion 220A of the substrate 220. The second and third interfacing features 208, 209 can comprise any suitable interfacing feature. For example, the third interfacing feature 209 can comprise a microstrip antenna to provide wireless communication between the sensor module 201 and an external computing device, such as a laptop computer, a mobile smartphone, a tablet computer, a docking station, etc. As one example, the third interfacing feature 209 can comprise a 2.45 GHz antenna for communication with a smartphone, laptop, tablet computing device, etc. As shown in FIG. 11, the third interfacing feature 209 can be disposed away from and orthogonal to the user's finger when the sensor module 201 is attached to the finger. Disposing the third interfacing feature 209 away from the user's skin can improve the operation of the interfacing feature 209. In some embodiments, the second interfacing feature 208 can comprise a wireless interfacing feature or a capacitive touch sensor, as explained above. For example, the second interfacing feature 208 can comprise a near field communications (NFC) antenna for near field authentication of the sensor module 1 and/or the larger sensing device to the user.

Figure 14:
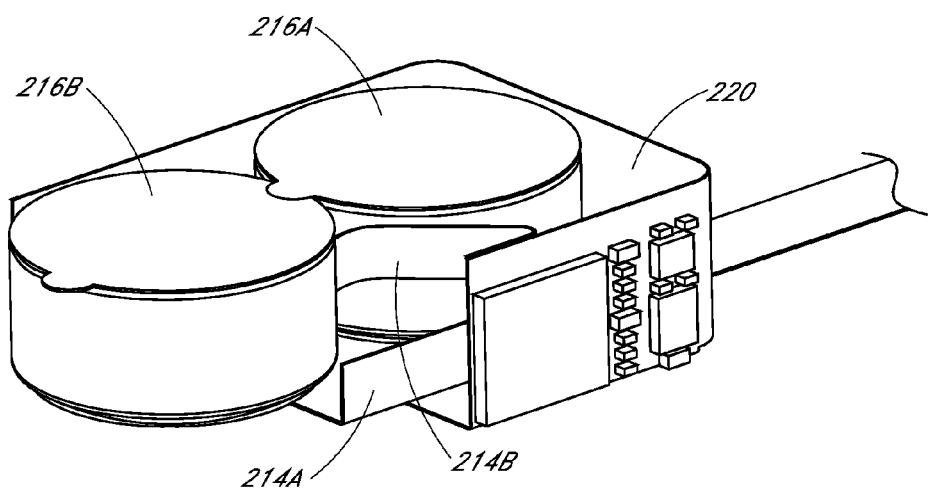
FIG. 14 is a perspective view of the batteries connected with the substrate.

FIG. 14 is a perspective view of the batteries 216A, 216B connected with the substrate 220, with the battery housing 202 omitted for purposes for illustration. The batteries 216A, 216B can electrically communicate with the first portion 220A by way of a first battery contact 214A and a second battery contact 214B. The first battery contact 214A can contact a first terminal of the batteries 216A, 216B (e.g., a negative terminal), and the second battery contact 214B can contact a second terminal of the batteries 216A, 216B (e.g., a positive terminal). The first and second battery contacts 214A, 214B can thereby enable the batteries 216A, 216B to supply power to the sensor module 201.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A sensor module comprising:
   a battery housing comprising a battery cavity sized and shaped to receive a battery, the battery cavity defined at least in part by a wall configured to be disposed about at least a portion of a periphery of the battery;
   a package housing disposed on the wall of the battery housing, the package housing smaller than the battery housing and comprising a package cavity;
   an integrated device package disposed in or coupled with the package cavity, the integrated device package comprising one or more integrated device dies;
   an interfacing feature coupled with the battery housing and extending transverse to the wall, the interfacing feature configured to transduce a biological signature into a signal to be processed by the integrated device package; and
   an interconnect assembly that electrically connects the interfacing feature to the integrated device package.

2. The sensor module of claim 1, wherein the interfacing feature comprises an electrode.

3. The sensor module of claim 1, wherein the interconnect assembly comprises a contact configured to electrically connect to an external device.

4. The sensor module of claim 3, wherein the contact is exposed on a bottom side of the battery housing by an aperture formed through the battery housing.

5. The sensor module of claim 4, further comprising a cover coupled with the battery housing over the battery cavity to define a top side of the battery housing, the cover comprising the interfacing feature.

6. The sensor module of claim 4, wherein the external device comprises the interfacing feature, the interfacing feature mechanically coupled to a platform on the bottom side of the battery housing, the interfacing feature electrically coupled with the contact through the aperture.

7. The sensor module of claim 1, wherein the package cavity is on a side of the wall opposite the battery cavity.

8. The sensor module of claim 1, further comprising a second interfacing feature coupled with the battery housing and extending transverse to the wall, the second interfacing feature disposed on a side of the battery housing opposite the interfacing feature.

9. The sensor module of claim 8, wherein the interfacing feature comprises a first electrode and the second interfacing feature comprises a second electrode.

10. The sensor module of claim 1, wherein the battery housing and the package housing comprise a unitary body.

11. The sensor module of claim 1, further comprising a third interfacing feature on an exterior surface of the integrated device package, the third interfacing feature comprising a capacitive touch sensor, an antenna, or an optical sensor.

12. The sensor module of claim 1, wherein the one or more integrated device dies comprises at least one of a processor die configured to analyze the signal to determine a heart rate of a user of the sensor module, a communications die configured to transmit data regarding the heart rate to an external computing device, and a motion sensor die to detect motion of a user of the sensor module.

13. A ring for measuring one or more biological signatures of a user, the ring comprising:
   a curved ring body sized and shaped to be worn by the user; and
   the sensor module of claim 1, the sensor module mounted to a support structure of the ring body.

14. A sensor module comprising:
   one or more housings sized and shaped to receive a battery;
   an integrated device package disposed in or coupled with the one or more housings; and
   an interfacing feature exposed on an exterior surface of the one or more housings and configured to transduce a biological signature into a signal to be processed by the integrated device package,
   wherein the integrated device package comprises a processor configured to analyze the signal and a wireless communications die configured to provide wireless communication with an external device, and
   wherein the sensor module is sized and shaped to have a volume less than about 3300 cubic millimeters.

15. The sensor module of claim 14, wherein the integrated device package comprises a motion sensor die configured to detect motion of a user.

16. The sensor module of claim 15, wherein the sensor module is sized and shaped to have a volume in a range of about 1500 cubic millimeters to about 3000 cubic millimeters.

17. A sensor module comprising:
   one or more housings sized and shaped to receive a battery having a battery volume $V_B$;
   an integrated device package disposed in or coupled with the one or more housings; and
   an interfacing feature exposed on an exterior surface of the one or more housings and configured to transduce a biological signature into a signal to be processed by the integrated device package,
   wherein the integrated device package comprises a processor configured to analyze the signal and a wireless communications die configured to provide wireless communication with an external device, and
   wherein the sensor module has a module volume $V_M$ that is larger than the battery volume $V_B$ by a factor K such that $V_M = K*V_B$, wherein the factor K is in a range of about 1.1 to about 3.5.

18. The sensor module of claim 17, wherein the factor K is in a range of about 1.5 to about 3.

19. The sensor module of claim 17, wherein the integrated device package comprises a motion sensor die configured to detect motion of a user.

20. The sensor module of claim 17, further comprising the battery.

* * * * *